United States Patent [19]

Jones

[11] 3,960,021

[45] June 1, 1976

[54] SAMPLING APPARATUS

[75] Inventor: Calvin Jones, Marlboro, N.Y.

[73] Assignee: Dairylea Cooperative Inc., Pearl River, N.Y.

[22] Filed: Oct. 4, 1973

[21] Appl. No.: 403,432

[52] U.S. Cl. .......................... 73/425.4 R; 81/3.1 R; 81/3.1 B; 81/3.46 R
[51] Int. Cl. .......................... G01n 1/12; B67b 7/16
[58] Field of Search ............... 73/425.4 R; 141/110; 224/45 A, 45 AA, 45 AB, 45 BA; 81/3.1 B, 3.3 R, 3.3 A, 3.46 R, 3.46 A, 3.1 R

[56] References Cited
UNITED STATES PATENTS

| | | | |
|---|---|---|---|
| 1,782,962 | 11/1930 | Hobbs............................... | 224/45 A |
| 2,624,201 | 1/1953 | Thomson ........................... | 73/425.4 |
| 2,645,957 | 7/1953 | Goldsmith.......................... | 81/3.3 A |
| 2,774,264 | 12/1956 | Bryant............................. | 81/3.46 R |

*Primary Examiner*—S. Clement Swisher
*Attorney, Agent, or Firm*—Curtis, Morris & Safford

[57] ABSTRACT

An apparatus for taking liquid samples, particularly milk, from containers thereof under substantially sanitary conditions is shown. The apparatus includes an elongated shaft having a handle and a decapping means associated with its upper part and a collar adapted to hold a sample vial extending from its lower part. Attached to an upper part of the shaft are means for removing, retaining and thereafter replacing a sample vial cap upon a sample vial without touching that vial cap. These means include a partial collar and a spring clip extending over that partial collar. The spring clip is adapted to urge the sample vial cap downwardly upon the upper surface of the partial collar and to retain it thereon while the sample vial is sanitized and thereafter filled with a sample of a liquid such as raw milk. With the apparatus of this invention, it is possible to avoid contamination of raw milk samples and to ensure that the samples taken are representative and that no contamination of the sample due to handling of the interior parts of the vial or the vial cap takes place.

18 Claims, 7 Drawing Figures

SAMPLING APPARATUS

This invention relates broadly to apparatus for taking liquid samples from containers under substantially sanitary conditions. More specifically, this invention relates to a manual sampling apparatus for taking samples of milk in sample vials without contaminating the sample vial or the cap thereof either before or after the sample is taken.

It is common practice in the milk collection and processing industry to take samples of raw milk produced on the farm in sample vials and store these for subsequent analysis in the laboratory. Typically, these samples are taken manually by tank truck operators or technicians from cans or similar containers of the raw milk, and the samples are taken at the farm location where the milk is collected. The samples are taken in small vials and are stored at low temperature until such time as analyses can be performed under laboratory conditions.

Procedures for sampling raw milk and analyzing the samples have been established by the United States Department of Health, Education and Welfare. These procedures permit a single sample of raw milk to be taken from a container thereof at the farm location and require that as many as fifteen or more analyses be made on that sample. Among these analyses are butterfat test, acidity test, direct microscopic count, catalase test, Standard Plate Counts, and so forth.

In order to take an accurate sample of the raw milk, the industry is faced with the problem of maintaining sanitary conditions within the sample vial used under the generally unsanitary conditions of the field locations where the samples are taken. The sampling devices taught in the prior art are generally unsatisfactory when used to sample raw milk because they are easily contaminated and the samples of milk taken are therefore not representative of the milk in the container being analyzed. Among the prior art sampling devices are that taught by W. M. Thomson in U.S. Pat. No. 2,624,201 and J. S. Losee in U.S. Pat. No. 2,236,063. Other sampling systems are that disclosed in N. Erickson, U.S. Pat. No. 1,108,561 and in F. V. Long et al., U.S. Pat. No. 2,598,183.

In attempting to develop a satisfactory sampling apparatus for use in the sampling procedures, applicant has recognized that certain advantages could be achieved using plastic vials and caps. These plastic vials and caps, typically which are made from polyethelene or other rigid or semi rigid plastics are manufactured at temperatures in the range of about 300° F and the vials are capped and sealed immediately after their manufacture. It has been demonstrated that the inside surfaces of the vials and the inside surfaces of the caps need no further sanitizing treatment. The sanitary characteristics of the surfaces are equal to the standards established for containers of finished milk products.

A more perplexing problem was encountered with respect to the outer surfaces of the sample vial and sample vial cap as well as the sampling apparatus itself. It is unacceptable to touch either the sampling apparatus or the outside of the vial prior to introduction of the apparatus and/or the sample vial into the body of raw milk. If these surfaces were contaminated with bacteria or other foreign matter, then this matter would be introduced into the milk, the milk itself would be contaminated and the sample would not be representative of the farmer's product. On the other hand, after the sample was taken, while it would not be acceptable to contaminate the inner surfaces of either the vial or the vial cap, the outer surfaces of the vial could be handled as could the apparatus itself, provided the apparatus was sanitized before being used again.

It is thus the primary object of this invention to provide an apparatus for taking liquid samples from containers thereof and particularly for taking samples of milk from cans or tanks thereof under substantially sanitary conditions.

It is a further and related object of this invention to provide a simple, inexpensive sampling device which may be used by tank truck operators or technicians to take samples of raw milk from containers thereof at field locations and to ensure that the samples are representative of the milk being sampled.

It is a further and related object of this invention to provide a readily sanitizable sampling device which in use will not contaminate the tank of milk being sampled and will secure a sample of milk into which no foreign matter or bacteria are introduced by handling.

It is still a further object of this invention to provide an apparatus for taking samples of milk under sanitary conditions which makes it unnecessary to touch the sample vial cap or the inside surfaces of the sample vial.

It is still a further object of this invention to provide an apparatus which is inexpensive to construct and is readily sanitizable, with smooth open contours which avoid crevices which otherwise could harbor contaminants against cleaning methods.

These and other objects of this invention are achieved in an apparatus for taking liquid samples from containers thereof under substantially sanitary conditions which includes an elongated shaft, a sample vial retaining means associated with the lower part of the elongated shaft and a means for removing a vial cap from the sample vial, retaining that cap and replacing that cap upon the sample vial, all without touching the vial cap, associated with the upper part of the elongated shaft. Desirably, the elongated shaft includes a comfortable handling means associated with its uppermost part. The sample vial retaining means may be a simple collar, sized to snugly hold the sample vial and may further include a foot extending outwardly from the shaft below the retaining collar. In the illustrated preferred embodiment, the decapping means (for removing a vial cap from the sample vial, retaining the cap and replacing the cap upon the sample vial, all without touching that sample cap), includes a partial collar which extends outwardly from the shaft and which has a configuration conforming substantially to the sample vial. The partial collar has a width and breadth or other lateral dimension which is larger than the upper part of the sample vial and yet smaller than the width and breadth of the sample vial cap. Whatever the lateral configuration of the top of the sample vial, the partial collar does not describe an arc of more than 180° and desirably has an upper surface. Means are positioned above the partial collar to urge a vial cap downwardly upon the upper surface of the partial collar. Desirably, the upper surface of the partial collar has raised landings or a sloped surface to prevent the vial cap retained therein from falling out. The preferred means positioned above the partial collar to urge the vial cap downwardly is a spring clip having a convex lower surface, the distance between that convex lower surface and the upper surface of the partial collar being less than the vertical dimension of the rim of the vial cap.

The sampling apparatus is further described and preferred embodiments are shown with greater particularity in the drawings.

Figure 1:
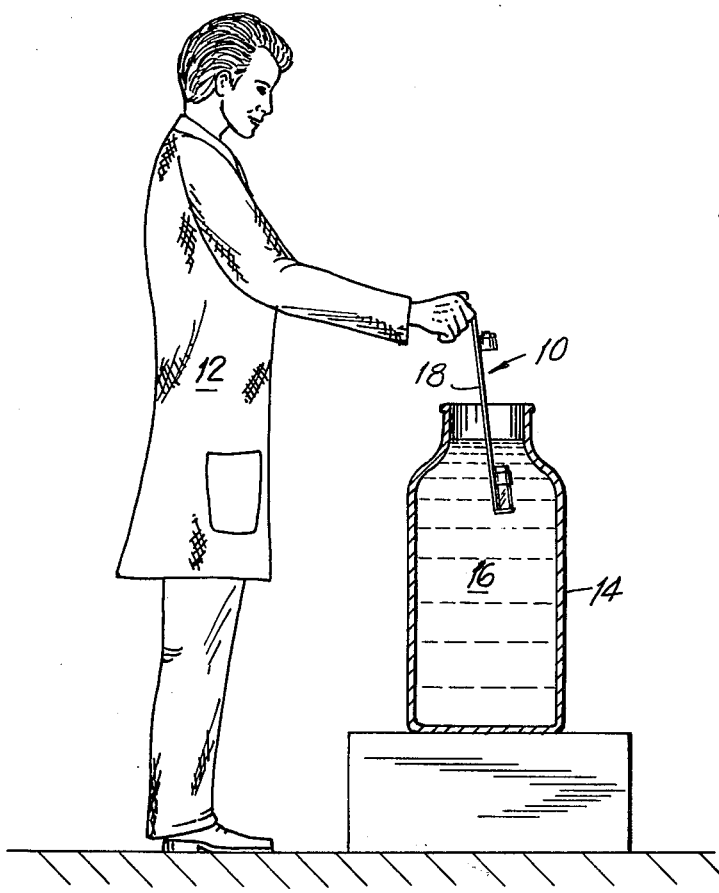
FIG. 1 shows a tank truck operator taking a sample of raw milk from a can thereof.
Figure 2:
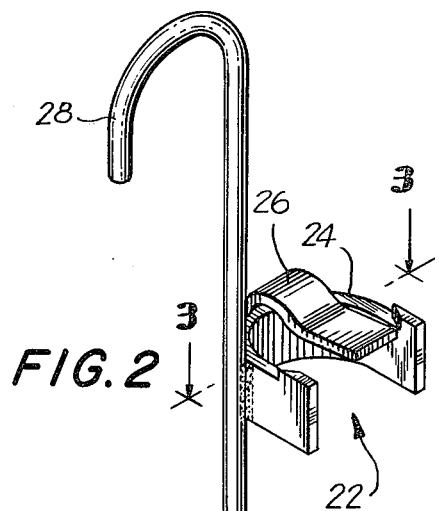
FIG. 2 is a view of the sampling apparatus showing the elongated shaft, the handle, the sample vial retaining collar at the lower part of the shaft and the means associated with the upper part of the shaft to remove, retain and re-emplace a sample vial cap upon a sample vial.

In FIG. 1 reference numeral 10 refers generally to the apparatus of this invention. The apparatus is being held by tank truck operator 12 and the sampling apparatus is shown immersed in a can 14 of raw milk 16. In FIG. 2, reference number 18 refers to an elongated shaft which desirably is formed of stainless steel. Connected to the lower part of shaft 18 is a substantially circular collar 20 which is sized to snugly hold a sample vial 48. Collar 20 may be of any suitable configuration matching that of the sample vial 48, i.e. it may be square, rectangular or have other lateral configuration. In the illustrated embodiment the collar 20 is formed from a flat ribbon of stainless steel which has been rolled into a circle with a very slight convex contour; so the center of the ribbon of steel is bowed inwardly (giving only a single line of contact between the collar 20 and the vial 48, held therein, yet not bowed enough to permit any wobble of the vial 48). The slight convexity of the collar 20 permits the innermost circumference thereof to be less than that of the vial 48; while the uppermost inner circumference is slightly larger than that of the substantially cylindrical vial 48, thus giving an easy lead-in and ensuring a snug fit. Additionally, the collar 20 may be slightly out-of-round without detriment. In fact this would reduce the line of contact to about 2 or 3 points of contact between the vial 48 and the collar 20 thus making the subsequent sanitizing procedure (described below) even more effective.

Associated with the apparatus shown in FIG. 2 is a means 22 for removing, retaining and re-emplacing a sample vial cap 50 upon a sample vial 48 without touching the cap 50. It includes a partial collar 24 which describes an arc of less than 180° and thereby permits entry and exit of the sample vial 48 and sample vial cap 50 within it. Above the partial collar 24 is a spring clip 26 which is connected to the rear part of the partial collar 24 which in turn is welded or otherwise connected to the elongated shaft 18. At the top of shaft 18 is a handle 28 which, as shown, may be a simple return bend and at the lower end of the shaft is a foot 30 which prevents the sample vial from passing downwardly through the collar 20. Foot 30 may be a simple right angle bend.

Figure 3:
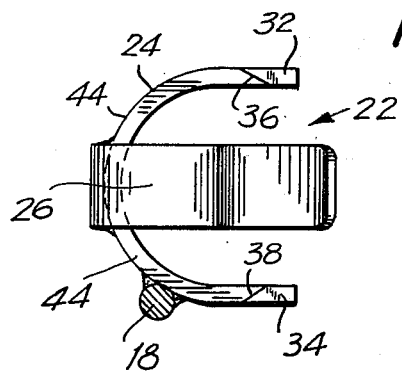
FIG. 3 is a plan view of the apparatus of FIG. 2 taken along lines 3—3 of FIG. 2.
Figure 3:
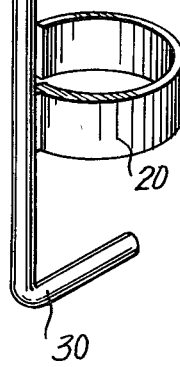
Figure 4:
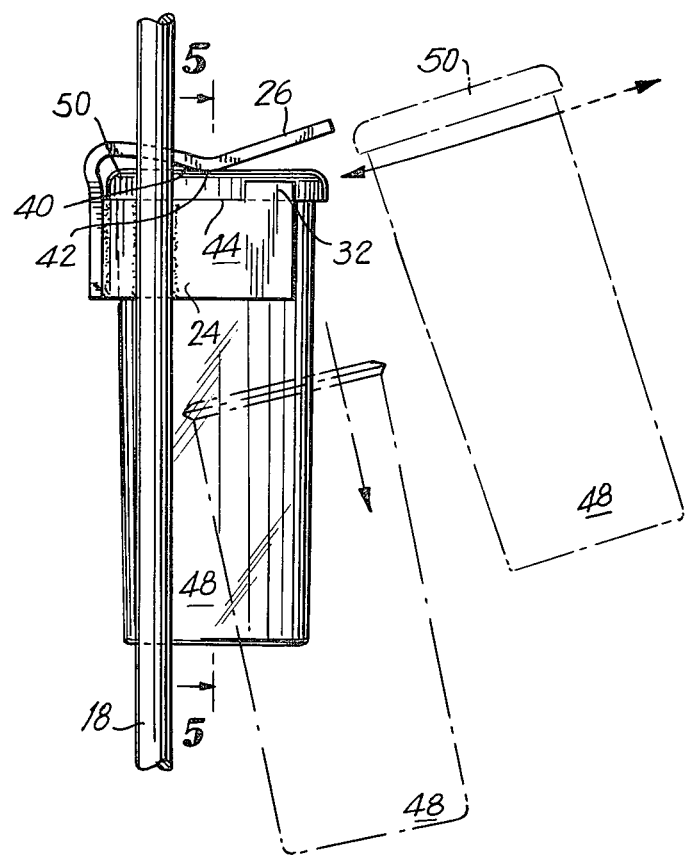
FIG. 4 is an expanded, side, vertical view of the apparatus of FIG. 2, showing a sample vial in its entry and retained positions.
Figure 5:
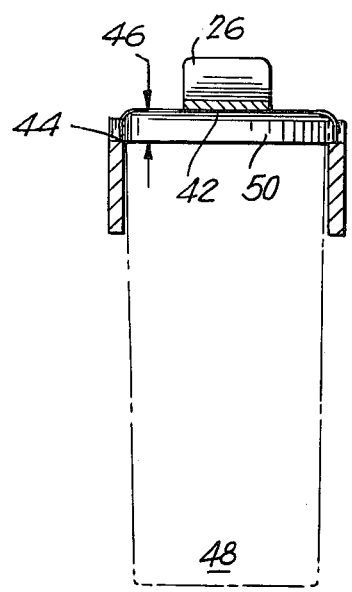
FIG. 5 is a rear, section view taken along lines 5—5 of FIG. 4.

As shown best in FIGS. 3, 4 and 5, partial collar 24 optionally has two raised landings 32 and 34 located on the upper forward parts of the collar. The purpose of these landings is to provide a positive catch behind the bottom lip of the vial cap 50 while the latter rests captured by clip 26 on the upper surface 44 of the collar 24 (thereby to prevent forward and outward motion of the vial cap 50 while it is being retained within means 22). Desirably, but not necessary the rear inner corners of the landings are chamferred as shown in FIG. 3 at reference numerals 36 and 38, in order to conform to the circumference of the cap 50 and to facilitate entry of the sample vial cap into means 22.

Spring clip 26 has a convex lower surface 40 which may be relatively uniformly convex or may have the pronounced convexity shown in FIG. 4. The purpose of this surface configuration is to permit easy entry and removal of the sample vial and cap into means 22. The distance between the lowermost surface 42 of spring clip 26 and the upper surface 44 of collar 24 is less than the vertical dimension 46 of the rim of the vial cap 50. Thus, spring clip 26 urges the vial cap 50 downwardly and forces it against upper surface 44 of collar 24 (and causing it to snap in behind the raised landings 32 and 34) thereby retaining the vial cap 50 within means 22. As shown best in FIG. 5, the inner diameter of collar 24 is larger than the corresponding diameter of vial 48 but is smaller than the outer diameter of vial cap 50. Having this configuration, it can be seen from FIGS. 4 and 5, that a vial 48 having a cap 50 thereupon can be pushed relatively easily into collar 24 and that spring clip 26 forces cap 50 downwardly on the upper surface 44 of collar 24 and retains the cap thereupon when vial 48 is pulled downwardly and outwardly away from the apparatus. Spring clip 26 in engaging and depressing the center of the vial cap 50, may also tend to flex outwardly the lower outer lip 51 of said cap 50 thereby partially disengaging the cap 50 from the vial 48 (and its corresponding raised lip 49) facilitating the decapping procedure. When vial 48 is reintroduced into collar 24 from below, cap 50 is reseated thereupon and the capped vial is firmly closed upon removal simply by exerting upward pressure on spring clip 26 and moving the capped vial outwardly in the direction from which it first entered.

Figure 6:
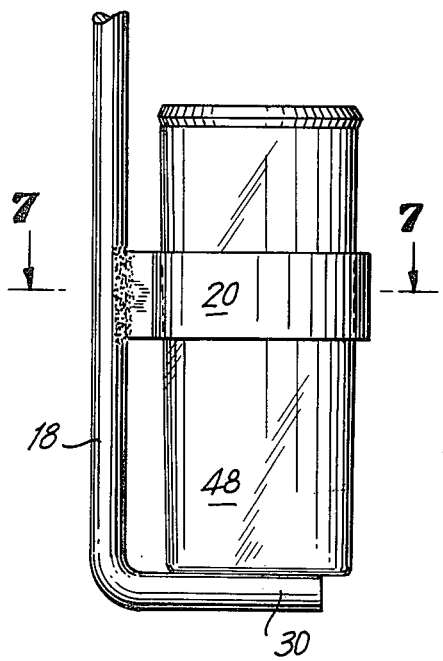
FIG. 6 is an expanded, side elevation view of the sample vial retaining collar associated with the lower part of the apparatus of FIG. 2.
Figure 7:
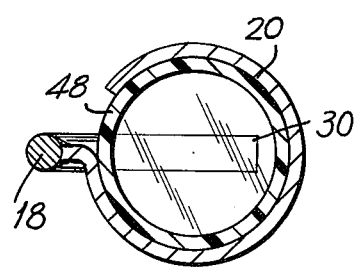
FIG. 7 is a top, sectional view, taken along lines 7—7 of FIG. 6.

FIGS. 6 and 7 show the lower end of elongated shaft 18 and show the details of circular collar 20. Foot 30 at the lower end of shaft 18 prevents vial 48 from passing through collar 20 and in a preferred embodiment, the distance between foot 30 and the upper portion of collar 20 establishes a fill level for the sample vial which can be visually controlled by the tank truck operator by adjusting the angle at which he removes apparatus 10 from the container 14 of raw milk 16. As shown in FIG. 7, collar 20 describes a less than full circle. In this configuration, it has a spring characteristic which provides a snug fit of vial 48 within it. Other configurations such as a "bicycle clip", etc. may also be used.

The apparatus shown in the drawings is preferably made of stainless steel and the collar and partial collar may be attached by welding to the lower and upper parts of the shaft respectively. Both the retaining collar 20 and the partial collar 22 can have dimensions and configurations corresponding to any cross-sectional configuration of a sample vial. The vial though illustrated as cylindrical, may be tapered or have an enlarged body with a cylindrical neck, or other configuration.

The apparatus of this invention is used as follows. When the tank truck operator desires to take a sample of raw milk from a container, he first takes a clean sample vial, which is capped and inserts it forwardly and downwardly into the partial collar 24 (from the dark-dot phantom outlined position of the capped vial to the full-lined position as shown in FIG. 4). The sample vial cap 50 is urged downwardly against the upper surface 44 of collar 24 and when the operator pulls (or unscrews) the sample vial 48 downwardly (see the uncapped dash-dot phantom outline of the vial 48 in FIG. 4), the sample vial cap is securely retained within collar 24. He then inserts the decapped vial within collar 20 and the sampler dipper and vial is inserted in a sanitizing solution containing chlorine in 200 ppm. or Iodophore solution 12 ppm. It is retained there for at least five minutes while the operator performs other functions such as weight recording, agitation of the tank, etc. Then the sampling apparatus, with the sanitized vial therein is removed from the sanitizing solution and the apparatus is immersed in milk and rinsed therein twice. After the third immersion, the sampler is removed at a preferred angle of about 30° so that when held upright the sanitized sample vial is approximately two-thirds full of milk. At no time during this procedure is the vial cap touched and it does not get immersed in the raw milk and therefore it retains the same sanitary characteristics that it had when it was manufactured.

At the end of the sampling procedure, the operator removes sample vial 48 manually from collar 20 and forces it upwardly and into collar 24, thereby forcing cap 50 back onto sample vial 48. By then urging vial 48 upwardly against spring clip 26, and moving it forwardly and outwardly in the direction it first came from, the recapped vial is removed from the sampling apparatus. At no time in the recapping of the vial is the cap touched by the operator's hands and, therefore, it again remains uncontaminated and the representative quality of the sample within the sanitized interior of the vial is ensured. The recapped vial containing the sample may then be rinsed and subsequently stored at a low temperature within an ice bath while it is being transported to a central laboratory for analysis.

Different types of sample vials and caps may be used in the apparatus including snap-on caps, screw caps and the like. Naturally, the vial retaining means and the decapping means would have to be modified accordingly.

What is claimed is:

1. An apparatus for taking liquid samples from containers thereof under substantially sanitary conditions comprising:
   a. an elongated shaft;
   b. means for retaining a sample vial associated with the lower part of said elongated shaft; and
   c. means for removing a vial cap from a sample vial, retaining said cap, and replacing said cap upon a sample vial, associated with the upper part of said elongated shaft.

2. An apparatus as recited in claim 1 wherein said elongated shaft includes handle means asssociated with its uppermost part.

3. An apparatus as recited in claim 1 wherein said means for retaining a sample vial associated with the lower part of said shaft includes a collar sized to snugly hold a sample vial extending outwardly from said elongated shaft.

4. An apparatus as recited in claim 3 wherein said means for retaining a sample vial further includes a foot extending outwardly from said shaft below said collar.

5. An apparatus as recited in claim 1 wherein said means for removing, retaining and replacing said vial cap includes
   a. a partial collar extending outwardly from said shaft and having a configuration conforming substantially to said sample vial with a width and breadth larger than those of the upper part of said sample vial and smaller than the width and breadth of the sample vial cap, and describing an arc of not more than 180°, said collar having an upper surface; and
   b. means positioned above said partial collar adapted to urge said vial cap downwardly upon the upper surface of said partial collar.

6. An apparatus as recited in claim 5 wherein the said upper surface of said partial collar has two raised landings located on the forward parts of said collar, said landings being positioned to prevent forward movement of said vial cap while it is urged downwardly upon said upper surface.

7. An apparatus as recited in claim 5 wherein the upper surface of said partial collar is higher in the forward part thereof than in the rear part thereof to impede forward movement of said sample vial cap.

8. An apparatus as recited in claim 5 wherein said means adapted to urge said vial cap downwardly upon the upper surface of said partial collar comprises a spring clip extending over the top of said partial collar.

9. An apparatus as recited in claim 8 wherein the vertical spacing between the upper surface of said partial collar and the lower surface of said spring clip is less than the vertical dimension of the rim of said vial cap.

10. An apparatus as recited in claim 9 wherein the lower surface of said spring clip is convex.

11. An apparatus for taking liquid samples from containers thereof under substantially sanitary conditions comprising:
   a. an elongated shaft having handle means associated with its upper part;
   b. a collar adapted to hold a sample vial extending from the lower part of said shaft; and
   c. means for removing, retaining and replacing a vial cap without handling said vial cap including
      1. a partial collar extending outwardly from said shaft and having a configuration conforming substantially to said sample vial with a width and breadth larger than those of the upper part of said sample vial and smaller than the width and breadth of the sample vial cap, said partial collar describing an arc of not more than 180° and having an upper surface, and
      2. a spring clip extending over said partial collar, the vertical spacing between the upper surface of said partial collar and the lower surface of said spring clip being less than the vertical dimension of the rim of said vial cap.

12. An apparatus as recited in claim 11 wherein the said upper surface of said partial collar has two raised landings located on the forward parts of said collar, said landings being positioned to prevent forward movement of said vial cap while it is urged downwardly upon said upper surface.

13. An apparatus as recited in claim 12 wherein the rear inner corner of the said landings are chamferred or squared to facilitate entry of the sample vial cap.

14. An apparatus as recited in claim 11 wherein the lower surface of said spring clip is convex to facilitate entry and removal of a sample vial and cap.

15. An apparatus as recited in claim 11 wherein said collar and partial collar are circular in configuration and a sample vial retaining foot is attached to said shaft below said collar.

16. An apparatus for removing a sample vial cap from a sample vial, retaining said cap and replacing said cap upon said vial comprising:
  1. a partial collar having a configuration conforming substantially to said sample vial with a width and breadth larger than those of the upper part of said sample vial and smaller than the width and breadth of the sample vial cap, said partial collar describing an arc of not more than 180° and having an upper surface, and
  2. a spring clip extending over said partial collar, the vertical spacing between the upper surface of said partial collar and the lower surface of said spring clip being less than the vertical dimension of the rim of said vial cap.

17. An apparatus as recited in claim 16 wherein the upper surface of said partial collar is higher in the forward part thereof than in the rear part thereof to impede forward movement of said sample vial cap.

18. An apparatus as recited in claim 16 wherein the lower surface of said spring clip is convex.

* * * * *